United States Patent
Nanda et al.

[11] Patent Number: 6,150,148
[45] Date of Patent: Nov. 21, 2000

[54] ELECTROPORATION APPARATUS FOR CONTROL OF TEMPERATURE DURING THE PROCESS

[75] Inventors: Gurvinder Singh Nanda; Rejean Laverdiere; Günter A. Hofmann, all of San Diego, Calif.

[73] Assignee: Genetronics, Inc., San Diego, Calif.

[21] Appl. No.: 09/176,136

[22] Filed: Oct. 21, 1998

[51] Int. Cl.[7] .................................................. C12N 13/00
[52] U.S. Cl. ...................................... 435/173.6; 435/285.2; 435/286.1; 204/547; 204/643; 935/87; 935/94
[58] Field of Search .............................. 435/173.6, 285.2, 435/286.1; 604/4, 20; 204/547, 643; 935/52, 85, 87, 89, 93, 94

[56] References Cited

U.S. PATENT DOCUMENTS

| | | | |
|---|---|---|---|
| 5,185,071 | 2/1993 | Serwer et al. | 204/299 |
| 5,422,272 | 6/1995 | Papp et al. | 433/287 |
| 5,676,646 | 10/1997 | Hofmann et al. | 604/4 |
| 5,869,326 | 2/1999 | Hofmann | 435/285.2 |

FOREIGN PATENT DOCUMENTS

| | | | |
|---|---|---|---|
| WO 91/18103 | 11/1991 | WIPO | C12N 15/87 |
| WO 98/10515 | 3/1998 | WIPO | C12M 3/00 |

OTHER PUBLICATIONS

G.S. Nanda et al., "Studies on Electroporation of Thermally & Chemically Treated Human Erythrocytes", 1994, 6 pgs.
S. Sukharev, et al., "Electrically–Induced DNA Transfer Into Cells, Electrotransfection in Vivo" 1994, 23 pgs.

*Primary Examiner*—David A. Redding
*Attorney, Agent, or Firm*—Baker & Maxham

[57] ABSTRACT

An electroporation method and apparatus generating and applying an electric field according to a user-specified pulsing and temperature profile scheme. The apparatus includes a cuvette holder with a Peltier device forming part of the electrode structures that form part of the holder. Advantageously, one such pulse includes a low voltage pulse of a first duration, immediately followed by a high voltage of a second duration, immediately followed by a low voltage of a third duration. The low voltage electroporation field accumulates molecules at the surface of a cell, the appropriately high voltage field creates an opening in the cell, and the final low voltage field moves the molecule into the cell. The molecules may be DNA, portions of DNA, chemical agents, the receiving cells may be eggs, platelets, human cells, red blood cells, mammalian cells, plant protoplasts, plant pollen, liposomes, bacteria, fungi, yeast, sperm, or other suitable cells. The molecules are placed in close proximity to the cells, either in the interstitial space in tissue surrounding the cells or in a fluid medium containing the cells.

31 Claims, 10 Drawing Sheets

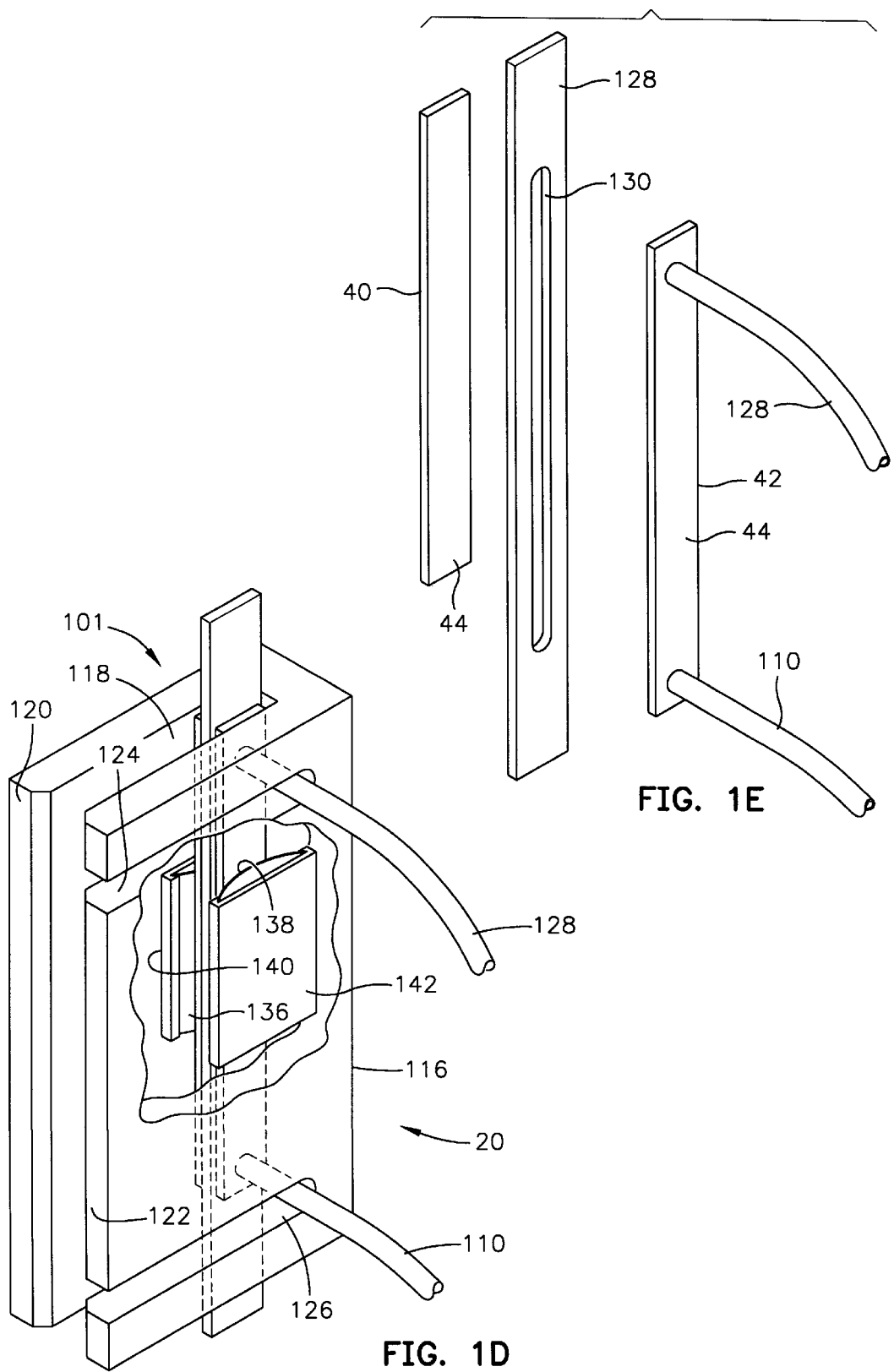

ELECTROPORATION APPARATUS FOR CONTROL OF TEMPERATURE DURING THE PROCESS

BACKGROUND OF THE INVENTION

1. Field of Invention

The present invention generally relates to electro-cell manipulation. More particularly, the invention concerns an electroporation apparatus and method for generating and applying an electric field to a material while controlling temperature of the process using a Peltier device for effective molecular introduction into cells and minimize damage to cellular tissue.

2. Description of Related Art

A cell has a natural resistance to the passage of molecules through its membranes into the cell cytoplasm. Scientists in the 1970s first discovered "electroporation," where electrical fields are used to create pores in cells without causing permanent damage to them. Electroporation was further developed to aid in the insertion of various molecules into cell cytoplasm by temporarily creating pores in the cells through which the molecules pass into the cell.

Electroporation has been used to implant materials into many different types of cells. Such cells, for example, include eggs, platelets, human cells, red blood cells, mammalian cells, plant protoplasts, plant pollen, liposomes, bacteria, fungi, yeast, and sperm. Furthermore, electroporation has been used to implant a variety of different materials, referred to herein as "implant materials," "implant molecules," "implant agents." Namely, these materials have included DNA, genes, and various chemical agents.

Electroporation has been used in both in vitro and in vivo procedures to introduce foreign material into living cells. With in vitro applications, a sample of live cells is first mixed with the implant agent and placed between electrodes such as parallel plates. Then, the electrodes apply an electrical field to the cell/implant mixture. Examples of systems that perform in vitro electroporation include the Electro Cell Manipulator ECM 600 product, and the Electro Square Porator T820, both made by the BTX Division of Genetronics, Inc. In San Diego, Calif.

Known electroporation techniques for both in vitro and in vitro applications apply a brief high voltage pulse to electrodes positioned around the effectuating region. The electric field generated between the electrodes causes the cell membranes to temporarily become porous, whereupon molecules of the implant agent enter the cells. In known electroporation applications, this electric field comprises a single square wave pulse on the order of 1000 V/cm, of about 100 $\mu s$ duration. Such a pulse may be generated, for example, in known applications of the Electro Square Porator T820, made by Genetronics, Inc.

U.S. Pat. No. 5,442,272 teaches of a quick connect suction electrode assembly for electroporation that includes a temperature regulating element. However, there is no suggestion to integrate temperature control with an electroporation control for efficient and effective implant material processing.

U.S. Pat. No. 5,185,071 teaches of a programmable electrophoresis apparatus using temperature controlling Peltier devices attached to the sides of a buffer chamber. This disclosure teaches only of electrophoresis applications.

Although known methods of electroporation may be suitable for certain applications, the electric field may actually damage the electroporated cells in some cases. For example, an uncontrolled electric field and generated heat may damage the cells by creating permanent pores in the cell walls. In extreme cases, the electric field may completely destroy the cell caused by overheating during an electroporation event.

Thus, existing electroporation systems may not be suitable for certain applications due to imprecise temperature control of implant agent materials and host cells during electroporation. Furthermore, many existing electroporation systems lack sufficient control over the parameters of the electric field pulses such as amplitude, duration, number of pulses during this process while simultaneously controlling the temperature of the implant materials.

SUMMARY OF THE INVENTION

Broadly, the present invention concerns an electroporation method and apparatus for generating and applying an electric field while controlling temperature according to a user-specified control scheme. An exemplary electroporation temperature controlling receptacle device includes a cuvette, a holder and a Peltier device for controlling temperature, the receptacle is configured for either static or flow conditions. The invention also provides for integrated control of the electric field for electroporation to move the molecule into the cell while controlling temperature of the implant agent and host cellular material. The implant agent molecular material may be genes or drugs such as DNA, portions of DNA, chemical agents or any other molecule. The molecular material is placed in close proximity to the cells in a fluid medium containing the cells.

Accordingly, one aspect of the present invention concerns a method of generating and applying an electric field according to a user-specified temperature control scheme integrated with an electroporation pulsing scheme for more efficient introduction of implant agents into cells and minimize damage to the cellular material.

The present invention provides a number of distinct benefits. Generally, the invention is useful to introduce molecules of an implant agent into cells with significantly increased effectiveness. The implant agent, for example, may include drugs for treating cancer, kaposi's sarcoma, and a number of other diseases and conditions.

In addition, by using electroporation to open cells for receipt of molecules of an implant agent, the invention increases the efficacy of the agent. Consequently, less of the implant agent is needed, thereby being more economical. The invention also provides a number of other benefits, as discussed in greater detail below.

BRIEF DESCRIPTION OF THE DRAWINGS

The nature, objects, and advantages of the invention will become more apparent to those skilled in the art after considering the following detailed description in connection with the accompanying drawings, wherein:

FIGS. 1A, 1B, 1C, 1D, 1E and 1F are diagrams illustrating various features of an electroporation cuvette and flow through chamber holders that include Peltier devices for temperature control for a contained or flow-through condition during the electroporation process.

DETAILED DESCRIPTION OF THE PREFERRED EMBODIMENTS

Hardware Components & Interconnections

As mentioned above, one aspect of the present invention concerns an electroporation apparatus and method for processing implant agents into cells by generating and applying an electric field to these materials while controlling temperature during the processing with a user selected control scheme of temperature for efficient and effective introduction of these materials to minimize damage to cellular tissue. Precision temperature control of the processing is provided by an integrated Peltier device with the electroporation apparatus using processor control.

Figure 1A:
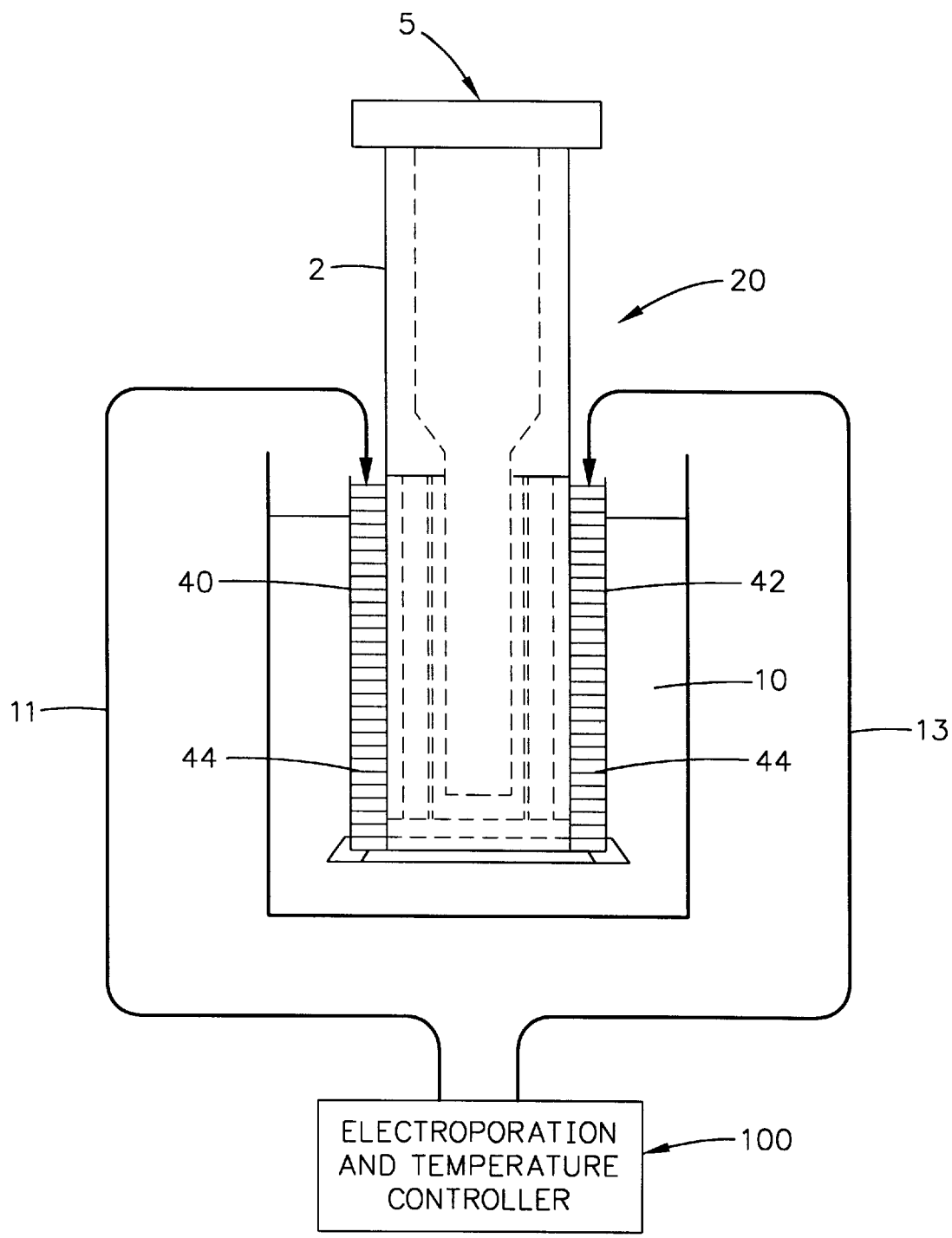
Figure 1B:
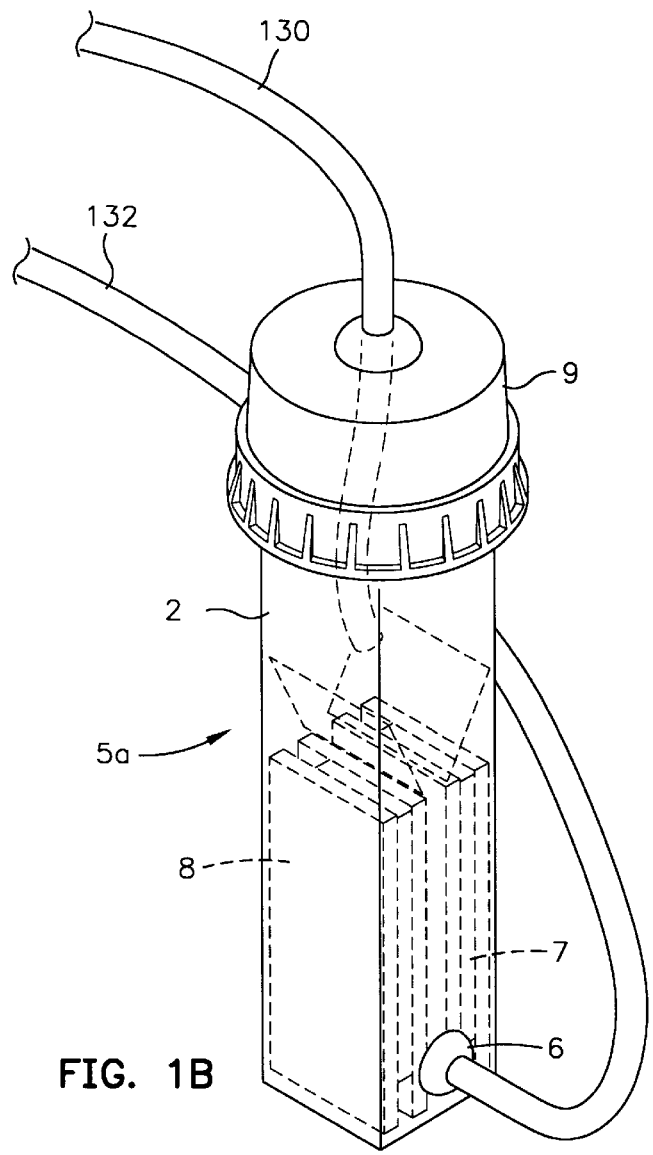

Receptacle: FIG. 1A illustrates a first preferred exemplary embodiment of the invention showing in cross-section a cuvette 5 which is a receptacle for both host cells and implant materials undergoing electroporation. FIG. 1B illustrates an alternate exemplary embodiment using a flow through cuvette 5a, which comprises a clear plastic rectangular housing defining an enclosure 9 having a round opening at the upper end. This is similarly taught in U.S. Pat. No. 5,676,646 entitled "Flow Through Electroporation Apparatus," which is incorporated by reference. Both of these receptacles can be in disposable-form. An example of the cuvette is BTX brand cuvette, model number 640 made by Genetronics, Inc. of San Diego, Calif. The cuvette 5 is portable and can be insertable into a cuvette holder 10. The cuvette holder is a platform, which supports the cuvette 5 for electroporation processing and electrically interfaces with electroporation and temperature controller 100.

This opening is closed by a push-on plastic cap 9. The tubing segment 130 extends snugly through a hole in the middle of the cap 9 at one end of the chamber. The tubing segment 132 extends through a hole in the lower end of the enclosure 2 which is sealed with a fitting 6. The enclosure 2 is preferably molded with a pair of embedded elongated electrodes 7 and 8 which that interface with the electrodes 40, 42 of the holder in a preferred form that carry the electrical signal from the electroporation and temperature control assembly 100. The electrodes 7 and 8 are uniformly spaced apart and extend parallel, substantially the full length of the receptacle 5a, between the inlet and outlet to enable fluid to pass therebetween. The electrodes (7 and 8) and (40 and 42) may be of any suitable conductive material such as stainless steel or aluminum and may be gold plated.

Receptacle Holder: The holder 10 (FIG. 1A) in exemplary form is an electrically insulated platform with terminals for connecting at least two independent conductors 11, 13 for supplying the electrical energy for both the electroporation pulses and causing the Peltier devices 44 to transfer heat energy to or from the receptacle and holder assembly 20. The holder device 10 is typically made of delrin or other nonconducting material with a screw clamping member for placement of a cuvette 5 or 5a in the holder 10. The electrodes 7,8 preferably interface with a pair of electrodes 40, 42 attached to the holder 10, but can be integrated in a single unit if required. An example of such a cuvette holder without components for regulating temperature is a BTX brand Safety Stand model 630-B made by Genetronics, Inc. of San Diego, Calif. Such a holder can also include an electrical safety interlock feature incorporated into a hood covering member to prevent electrical shock to personnel when operated.

The holder 10 preferably uses a plate-shaped electrodes 40, 42 with Peltier devices 44 incorporated therein that allows for rapid heating or cooling of host and implant materials in the cuvette. The Peltier device 44 contained in the electrodes 40, 42, control temperature of materials undergoing electroporation. The holder preferably includes a temperature sensor 58 (FIG. 2B) that is attached to or in close proximity to materials undergoing electroporation. In particular, the temperature sensor 58 can be attached to the holder 10 for maintaining close proximity to the cuvette during processing to provide closed-loop processing temperature control in real-time. The temperature sensor 58 can be, for example an infrared temperature sensor that is attached to a hood member of the holder 10 such that when closed, accurate temperature measurement of the material undergoing electroporation is achieved.

Before electroporation begins, the receptacle receives cellular and implant materials for in vitro use, the materials are cells and implant agent materials placed in either form of the cuvette 5 or 5a. The operation entails having a technician inject a liquid implant agent by pouring, eye-dropping, or otherwise introducing the agent into the cuvette using automated equipment for dispensing these materials.

Figure 1C:
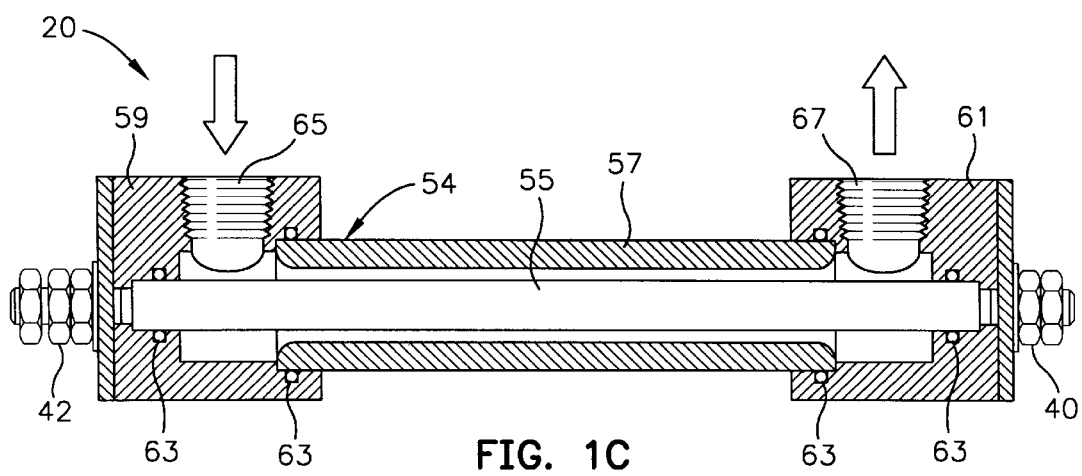

Flow-Through Receptacle: FIG. 1C illustrates another embodiment of the receptacle device in a flow-through chamber 54 form. This receptacle device is taught in U.S. Pat. No. 5,676,646 entitled "Flow Through Electroporation Apparatus," except for the means for controlling temperature of the materials. The chamber 54 receptacle device receives cellular and implant materials for in vitro use by withdrawing fluids from a reservoir or human for processing during transmission. The flow through receptacle and holder unit 20 comprises a rectangular outer housing 57 which encloses an elongated flow through chamber 54. It includes a pair of uniformly spaced apart elongated electrodes in the form of a cylindrical conductive rod 55 concentrically mounted with a cylindrical vessel 57 defining opposed parallel electrode surfaces. Preferably, the rod 55 and vessel 57 are made of stainless steel and may be gold plated where desired. The ends of the electrode surface forming rod 55 and vessel 57 are mounted in hollow blocks 59 and 61 of insulating, plastic material and sealed with high temperature elasticomeric O-rings 63. The O-rings are seated within circular groves machines inside the blocks 59 and 61. They are preferably made of a high temperature resistant material such as that sold under the trade mark of VITON.

The blocks 59 and 61 have cylindrical holes bored therein for receiving the ends of the rod 55 and vessel 57. The blocks 59 and 61 have inlet and outlet ports, 65 and 67, respectively formed therein so that the mixture of a blood and fluid medium can pass through the flow through chamber between the opposed electrodes as indicated by the arrows (FIG. 1C). Fittings 71 and 72 (FIG. 2A) are screwed into the threaded walls of the inlet and outlet ports at 65 and 67 for coupling tubing segments 74 and 76 thereto. The tubing segments 74 and 76 extend within the housing 52 and are in turn connected to fitting 78 and 80 mounted on the front panel of the housing. The tubing segments 130 and 132 are connected to the fittings 78 and 80, respectively.

The electric cables 136 and 138 (FIG. 2A) from the electroporation and temperature subsystem 100 have plugs that are removably connected to jacks 82 and 84 on the front panel of the housing 52 of the flow through chamber unit. These jacks are in turn connected to wires 86 and 88 which connect to threaded shaft and nut electrode assemblies 40 or 42 (FIG. 1C) as one electrode and to a clamp around vessel 57 as the other electrode of the flow through chamber 54. The electrode nut assembly 40 and 42 provide an electrical connection to the rod electrode 55 while the assembly 42 provides an electrical connection to the vessel electrode 57. The Peltier devices 44 are mounted to the external ends of the nut electrode structures 40 and 42.

FIG. 1D shows another embodiment of a flow through chamber receptacle holder 101 that can be used with a peristaltic pump (not shown) with an input receiving tube 110. This is taught in U.S. Pat. No. 5,676,646, except for components for controlling temperature of the materials undergoing electroporation. This flow through electroporation chamber receptacle includes a safety stand 116, having a generally U-shaped configuration with a slot 118 for receiving the disposable chamber formed between opposing sides, or thermally conducting panels 120 and 122. The side panel 122 is provided with upper and lower slots 124 and 126, respectively, for receiving the fluid or tubes 110 and 128 connected to the chamber.

FIG. 1E shows the chamber, within which, the materials undergoing electroporation pass through comprises a central generally rectangular bar-shaped body member 128 having an elongated centrally disposed through slot 130 formed therein as shown in FIG. 1D. The slot 130 is enclosed on opposite sides of the bar-shaped body member 128 by means of a pair of bar shaped electrodes 40 and 42. The central body member 128 is preferably constructed of a non-conductive material whereas the bar electrodes 40 and 42 are preferably constructed of conductive material that can easily be gold-plated, at least along the surfaces, in communication with the sides of the slot. The electrode 134 is provided with upper and lower tube connections for attachment of the tubes 110 and 128 for opening communications directly with the upper and lower ends, respectively, the slot 130. The flow through chamber receptacle is assembled with the electrodes 40 and 42 with Peltier devices 44, sealingly engaging opposite sides of the bar 128 enclosing the slot 130. The electrodes are preferably, sealingly bonded by suitable means to the opposite sides of the central bar member. The assembled chamber then slides into the open slot 118 in the safety stand 116 between a pair of opposing spring contacts 136 and 138. These contacts are of a suitable conductive material, such as a copper alloy and are mounted in conductive holders 140 and 142, which are in turn attached to conductive cables.

Figure 1F:
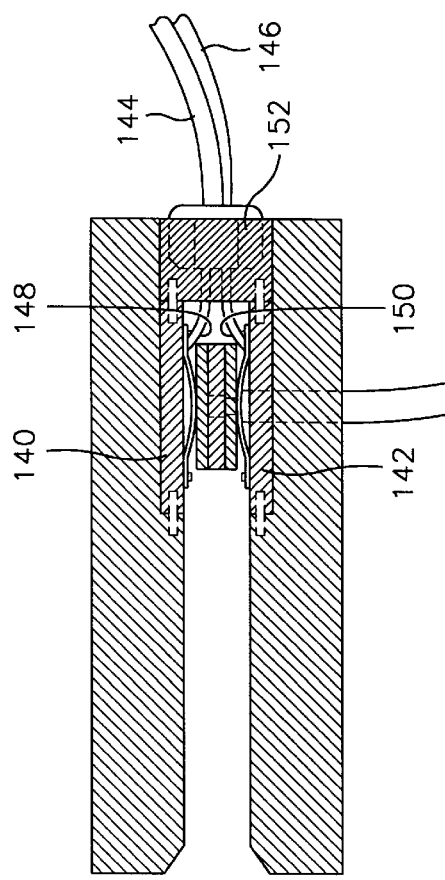

FIG. 1F shows the electrical cables in a top view 144 and 146 pass or extend through an opening 166 having a gromit 168 in the backplate 152. A pair of conductive cables, 144 and 146, include leads 148 and 150 connected such as by soldering to the respective holders 140 and 142. Spring contacts 136 and 138 may have any suitable construction, but in a preferred form is constructed to have a somewhat louvered configuration for proper thermal contact. A blower unit can also be incorporated if required.

Variations of the cuvette can be use of a concentric annular electrode structure wherein a center electrode would be at the center of the cuvette and an outer electrode would be on the surface of the cuvette. A variation of the holder 10 would include an electrode that attaches through the top center and center of the cuvette with an outer electrode interfacing with the cuvette which would contain the Peltier device 44. At least one Peltier device must be incorporated with the cuvette 5 or 5a and corresponding holder 10. Preferably, the electrodes 40, 42 provide heat flow control using the integrated Peltier device in each of the electrodes. Electroporation and Temperature Subsystem: An electrical pulsing field is placed across the material between electrodes 40, 42 as discussed above in the receptacle and holder assemblies 20. The electrode structures 40, 42 of these above embodiments receive electrical input from a separate power control 201 (FIG. 2B). Wires with low resistance are used to make the connection to electrodes 40, 42. An electrical field is formed between electrodes 40, 42 structures within the receptacle when the power supply is controllably turned on from the subsystem 100 to provide a pulsing electric field across the materials undergoing electroporation. Control of the electroporation pulsing scheme by an electric field which varies in both magnitude and duration improves transfection of gene material. The preferred electroporation pulsing scheme is taught in U.S. patent application Ser. No. 08/709,615, entitled "Electroporation User Configured Pulsing Scheme," which is hereby incorporated by reference.

In addition to providing an electrical pulsing scheme that is user-programmable, the present invention provides temperature control of the material that is undergoing electroporation which naturally warms or cools the materials contained within the receptacle when electric fields are transmitted therethrough. The receptacle and holder assembly 20 is equipped with a Peltier device 44 for the temperature control during the electroporation process. The Peltier device 44 is electrically and thermally junctured at the electrodes 40, 42. Peltier device 44 receives current from an external, feedback regulated power supply forming part of the subsystem 100. The Peltier device 44 controls temperature within <±0.1 C. Controlling material temperature during the electrical pulsing electroporation treatment provides an improved material yield.

Figure 2A:
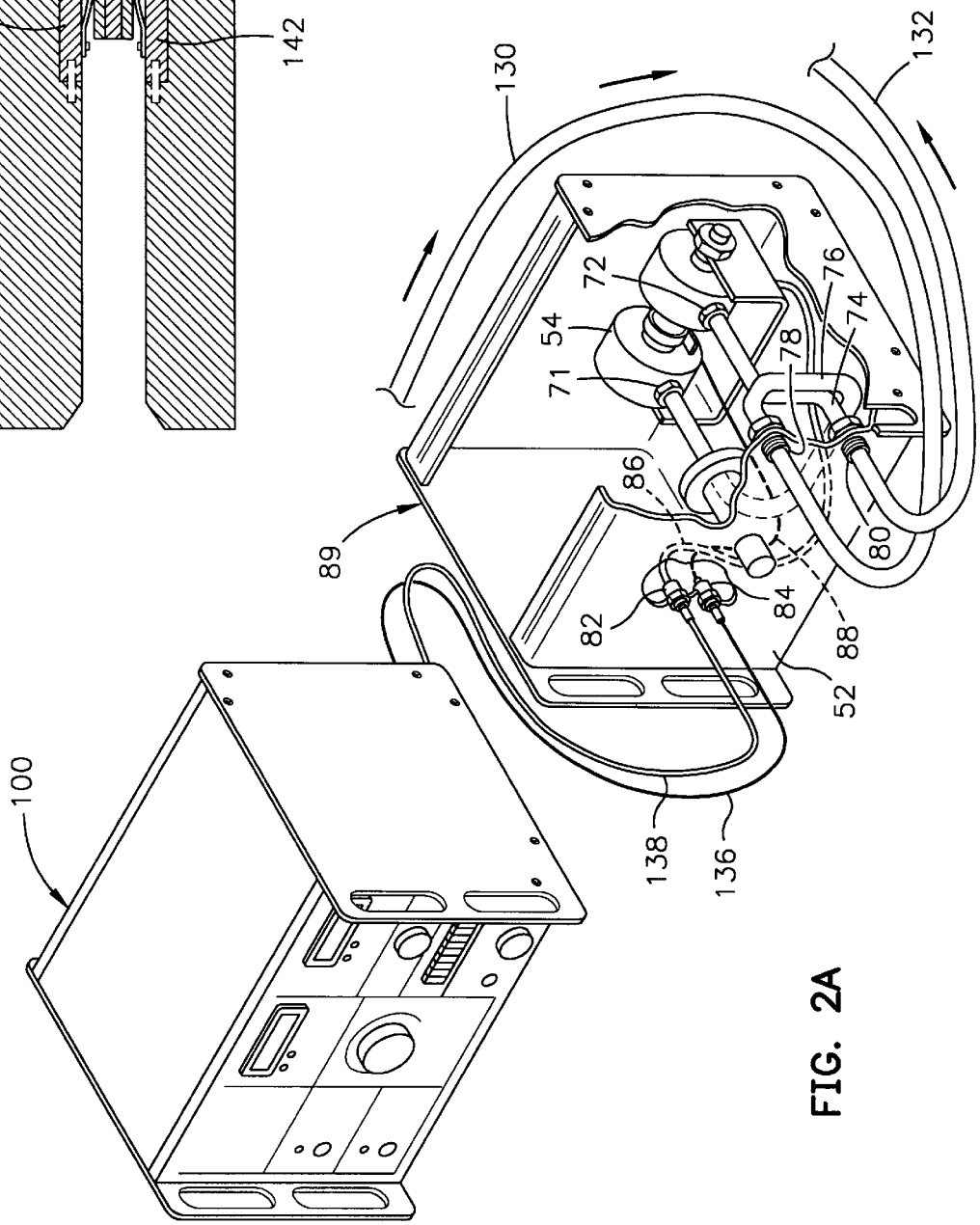
FIGS. 2A and 2B show the electroporation and temperature control hardware and interconnections to the receptacle holders in perspective and block diagram form pursuant to the present invention.
Figure 2B:
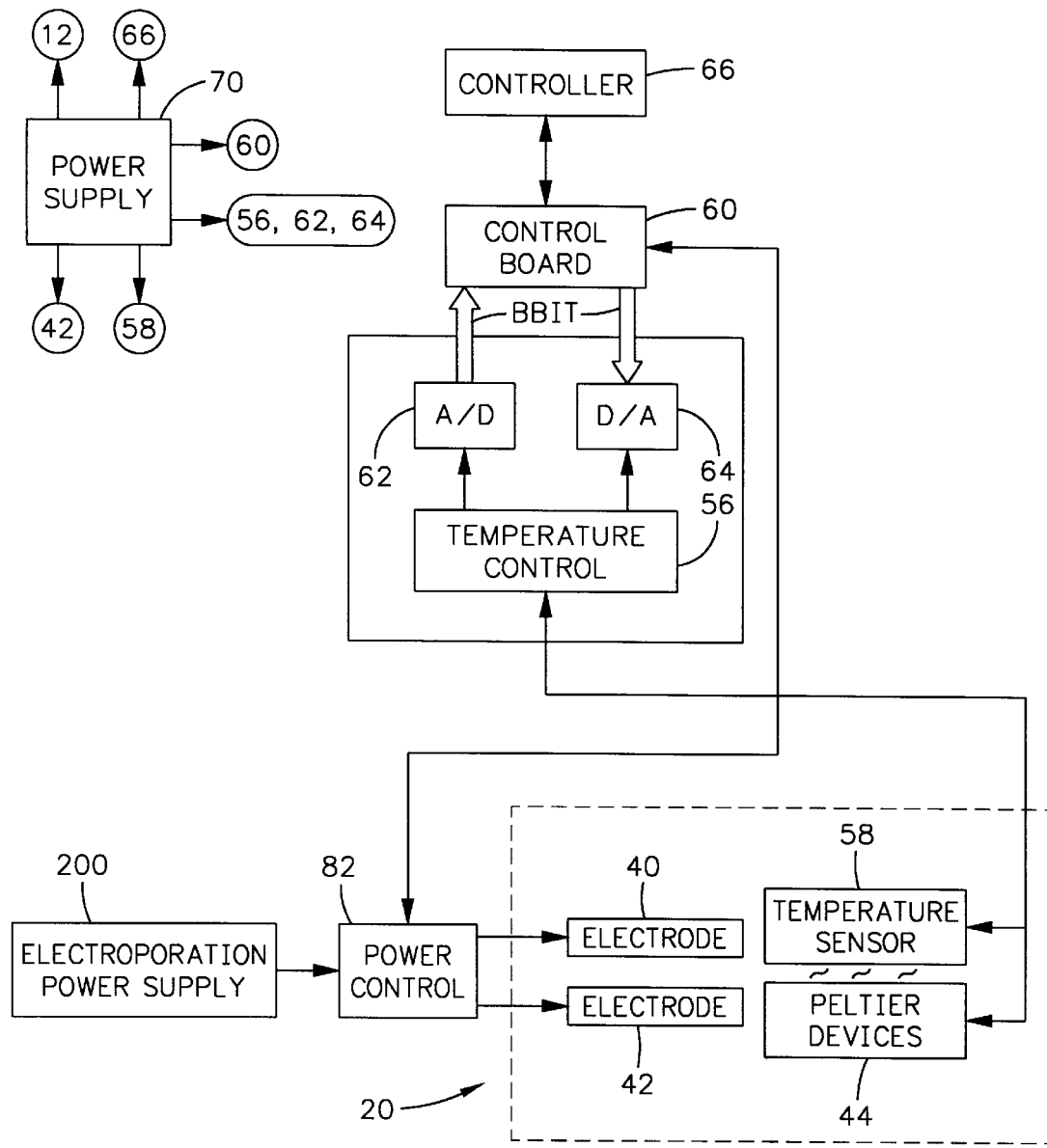

FIG. 2A shows an exemplary application of the apparatus that is used with a peristaltic pump (not shown), and injection pump (not shown), a flow through receptacle chamber receptacle assembly 89 and the electroporation and temperature control subsystem 100. This is similarly taught in U.S. Pat. No. 5,676,646 entitled "Flow Through Electroporation Apparatus," except for the means for controlling material temperature. The apparatus includes a pair of electric cables for connecting the subsystem 100 with the flow through receptacle assembly 89.

FIG. 2B illustrates a block diagram showing the components for controlling the pulsing field magnitude, field duration and temperature control of the cuvette holder 10 with receptacle device. Beginning with temperature control, the Peltier device 44 forms part of the electrode structures for receiving electrical input from temperature control block 56. Upon receiving electrical current from temperature control 56, the Peltier device transfers heat from the adjacent material within the receptacle to its external surface within the assembly 20. A temperature sensor may be used to communicate with the material undergoing electroporation to provide feedback signals to temperature control 56.

Temperature sensor 58, which can be an infrared type sensor, receives temperature readings from the material in the electroporation cuvette holder device 10 and sends corrective signals to temperature control block 56 which then responds with an appropriate electrical signal to Peltier device 44.

Temperature control block 56 functions to send an output electric signal to device 44 in response to temperature sensor input. The output of temperature sensor 58 is fed into an amplifier. The amplifier, can be contained within the analog portion of the temperature controller 56. Also, within temperature controller 56 is a comparator which receives the amplified signal and which functions to compare the amplified signal with an operator-initial or a reference signal sent through a digital-to-analog converter to the comparator. When the temperature is above the reference, the output from the comparator forward biases a power transistor with ratings of less than 100 amps and 100 volts which is connected in series with the Peltier device 44, thereby allowing cooling of materials in the cuvette or flow through receptacle. Conversely, heating can occur by reversing directional current through the Peltier device 44 by having a symmetrical connected type circuit attached to the electrode structures. To provide information for the control board, an amplified signal from temperature sensor 58 is sent to an analog to a digital converter and is used for reporting. This signal could, however, also be used for control through the user's program. Temperature control 56 is regulated by control board 60 that is digital-based. The control board 60 interfaces to the analog-based control 56 via analog/digital converter 62 and digital/analog converter 64 (FIG. 2B).

Control board 60 functions to control temperature of the material undergoing electroporation. The control board 60 receives its program from a controller 66 and, once the program is entered, the keyboard and the computer are no longer necessary. Programming can be in computer languages such as C or BASIC (registered trade mark) if a personnel computer is used for the controller or assembly language if a microprocessor is used for the controller 66. A user specified control of temperature is programmed in the controller 66.

The controller 66 may comprise a computer, a digital or analog processing apparatus, programmable logic array, a hardwired logic circuit, an application specific integrated circuit ("ASIC"), or other suitable device. In an exemplary embodiment, the controller 66 may comprise a microprocessor accompanied by appropriate RAM and ROM modules, as desired. The controller 66 is coupled to a user interface 50 for exchanging data with a user. In the illustrated example, the user may operate the user interface 50 to input a desired pulsing pattern and corresponding temperature profile to be applied to the electrodes 40, 42 and Peltier device 44. The voltage polarity controls direction of heat flux to or from the receptacle device and current output to the Peltier device 44 can be either amplitude or pulse width modulated for precision heat flux control.

As an example, the user interface 50 may include an alphanumeric keypad, touch screen, computer mouse, push-buttons and/or toggle switches, or another suitable component to receive input from a human user. The user interface 50 may also include a CRT screen, LED screen, LCD screen, liquid crystal display, printer, display panel, audio speaker, or another suitable component to convey data to a human user. Controller 66 used for inputting and outputting signals to control board 60 may be any type of ASCII terminal having an RS-232 or RS-485 port. The control board which receives input from the computer and produces outputs, can include an 8052-AH-BASIC microprocessor (8 Kb BASIC ROM, a programmable pulse generator, built-in algorithm using EEPROMs and EPROMs) 8 Kb of RAM, 8 Kb of battery-backed RAM, battery-backed real-time clock and timer with 0.005 sec resolution, 8 Kb of ROM command extensions, 8 Kb of EEPROM, 24 bits of programmable digital input-output, and an RS/232 printer port with a programmable Baud rate.

Control board 60 functions to receive controller 66 input and is driven by the power supply 70. Power supply 70 is a switching type which can have the following typical outputs: 12 volts with up to 20 amp output to the Peltier device 44, the RS-232 or RS-485 port, the digital to analog converters 62 and 64, and temperature control block 56. Power supply 70 also provides −12 volts, 0.25 amps for the RS-232 port and the temperature control block. Additionally, power supply 70 would typically supply 5 volts and one amp to the control board 60 and the temperature control 56.

Figure 3:
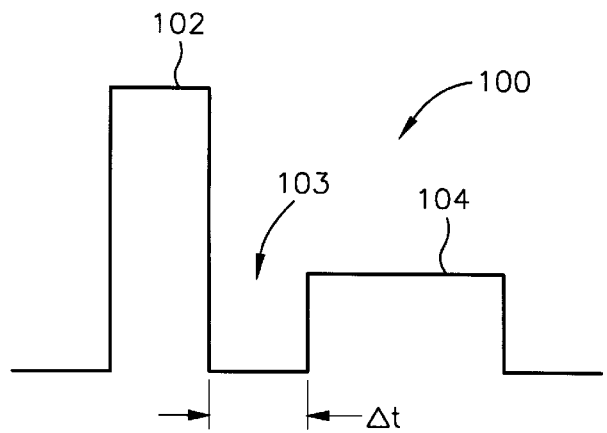
FIG. 3 is a diagram illustrating an electroporation waveform known in the art.

Electroporation Pulsing Subsystem: FIG. 3 (PRIOR ART) shows a pulsing scheme for electroporation as known in the art. To generate such a pulse, Prior electroporation power supplies used electromechanical relay to provide consecutive e first and second pulses, see S. I. Sukharev et al., Biophys. J. Vol. 63, November 1992, pp. 1320–1327. More particularly, Sukharev uses an electric field pulse 101. The pulse scheme 101 includes (1) a first, narrow duration, high voltage pulse 102, (2) a delay 103 of Δt, during which no pulse is generated, then (3) a second, wide duration, low voltage pulse 104. The first pulse 102 was intended to porate the membrane, whereas the second pulse 104 was intended to electrophorese DNA into the cell cytosol. Sukharev recognized that the delay 103 should not be excessive.

Although the Sukharev system may provide satisfactory results in some applications, this system may not be completely adequate for certain other applications. Some users may find, for example, that Sukharev's electroporation does not effectively move enough molecules of the implant agent into the target cells. This results from an excessive delay 103 between Sukharev's first 102 and second 104 pulses, as recognized by the present inventor. The pores of a cell, created by electroporation, stay open for a finite time, largely depending upon the cell's temperature. Thus, the effect of the first pulse may start to significantly decay (thereby closing the cell's pores) during the delay between the first and second pulses. In some applications, this may be sufficient to completely nullify the first pulse's effect upon the cell by the time the second pulse occurs. As a result, the efficacy of Sukharev's electroporation may be insufficient in some cases. Moreover, lacking an effective first pulse, the second pulse of Sukharev's system may need to be increased to the point where it permanently destroys cells.

The delay described above is inherent to the Sukharev system due to the use of electromechanical relays. Sukharev uses independent pulse generators, whose outputs are selectively coupled to output electrodes by a relay. As known in the art, however, the switching of an electromechanical relay typically takes a significant amount of time, sometimes even 50–100 ms. Therefore, the efficacy of the implant agent achieved by Sukharev may be too low for some applications.

Figure 4:
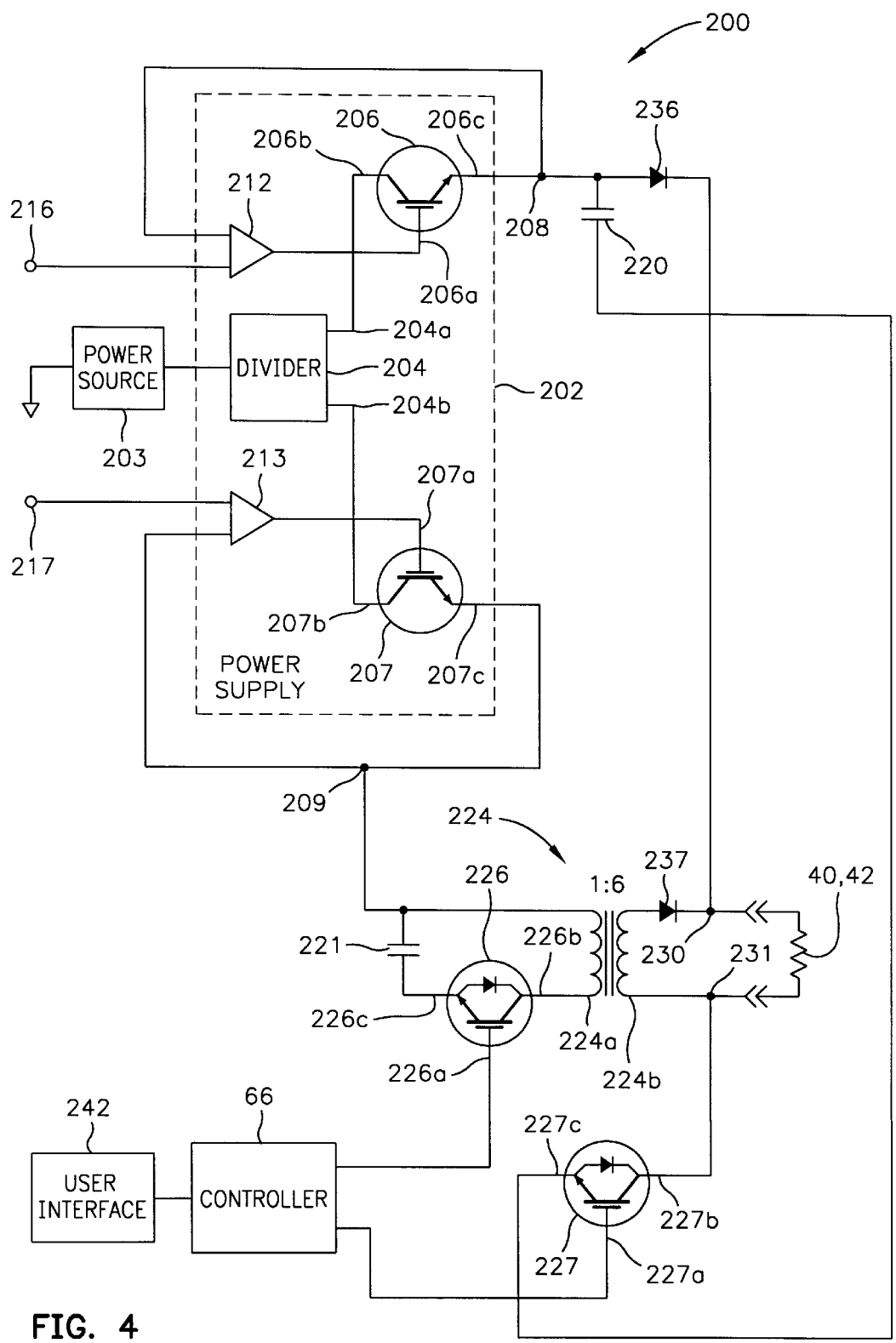
FIG. 4 is a diagram of an exemplary hardware components and interconnections of an electroporation pulse controller and generator subsystem pursuant to one aspect of the present invention.
Figure 8:
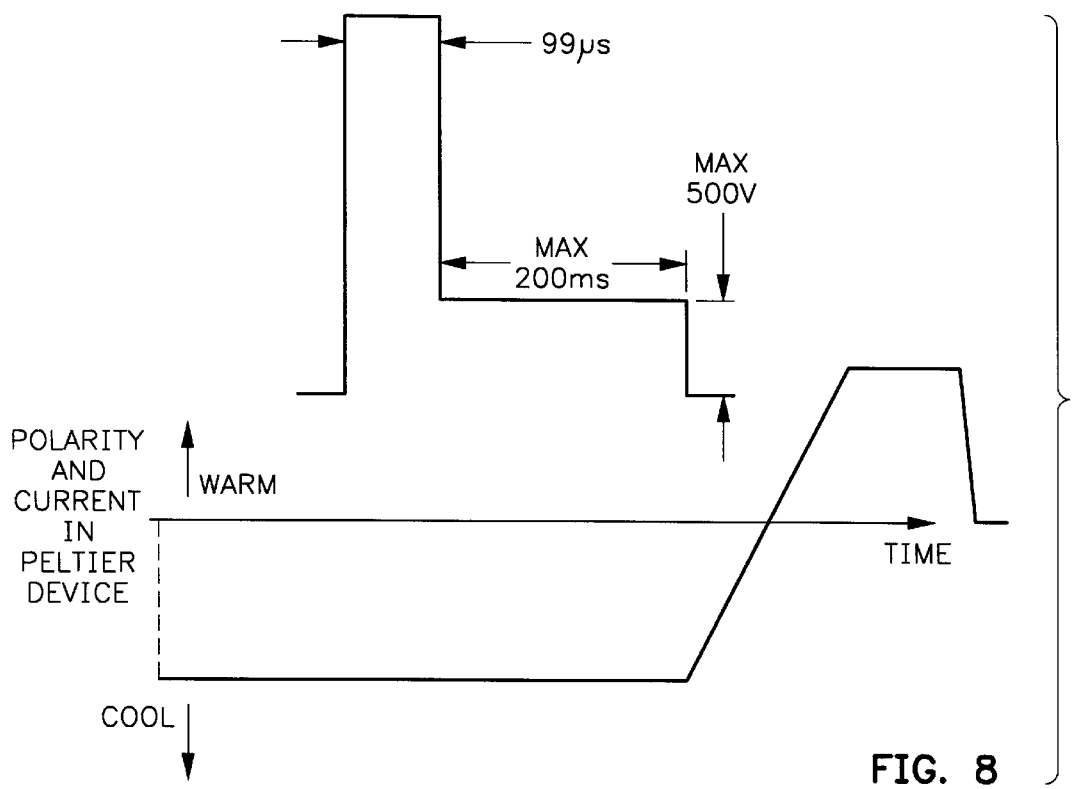
FIGS. 8–11 are drawings of illustrative electroporation pulsing schemes with temperature control, pursuant to the invention.

Electroporation Power Supply: FIG. 4 shows the pulsing electroporation power subsystem 200 which receives an input voltage, such as 110V or 220 VAC, from a power source 203. Preferably, the subsystem 200 includes a comparable apparatus, which is disclosed in U.S. patent application Ser. No. 08/709,615 and entitled "Electroporation User Configured Pulsing Scheme.". The subsystem 200 has an electroporation power supply 202 and driver control 204 which controls or changes voltage magnitude, switch on or off, invert voltage polarity or provide voltage pulsing from the power supply 202 to electrodes 40, 42. Signals from control board 60 control provide the desired voltage or current output. A power supply 202 provides a reliable source of desired voltage levels for use by the electroporation power control 201. An example of such a source is available, for example, from Electro Square Porator T820, made by the BTX Division of Genetronics, Inc. Either independent from or associated with power supply 70 is an electroporation power supply 202 which produces sufficient voltage range, preferably up to 500 volts. The divider 204 converts the input voltage into multiple reference voltages. In the illustrated embodiment, reference voltages of 500 V (D.C.) reside on the divider output lines 204a–204b.

These voltages are provided to collectors 206b–207b of first and second respective transistors 206–207. The transistors 206–207 are selectively gated to apply their input voltages to step voltage nodes 208–209. The selective gating of the transistors 206–207 is performed by respective comparators 212–213, which trigger gates 206a–207a of the transistors 206–207 when voltages at the step voltage nodes 208–209 dips below voltages established on step voltage input lines 216–217. For example, when the comparator 212 determines that the voltage on the step voltage node 208 is less than the voltage on the preset input line 216, the comparator 212 activates the gate 206a of the transistor 206, causing the transistor 206 to couple the input voltage of the divider 204 directly to the step voltage node 208. Thus, the transistors 206 maintain substantially constant voltages at the respective step voltage nodes 208–209 in accordance with the step voltage input lines 216–217.

Energy Reservoirs: The subsystem 200 also includes energy reservoirs 220–221 coupled to respective step voltage nodes 208–209. Exemplary energy reservoirs 220–221 may comprise capacitors, such as 3200 $\mu$F, 500 V electrolytic capacitors. These capacitors are appropriate for maximum step voltages 208–209 of 500 V (D.C.).

Transformer: The subsystem 200 also includes a transformer 224, which includes a primary winding 224a and a secondary winding 224b. The transformer 224 preferably is designed with low leakage inductance characteristics to provide a fast pulse rise time, i.e., several microseconds. Preferably, the transformer 224 exhibits low inductance, on the order of a few $\mu$H. These features may be provided by winding the transformer 224 with a single cable of twelve separate, twisted conductors of which six are connected in parallel for the primary, six are connected in series for the secondary. This provides a 1:6 step-up ratio. In addition, a separate low voltage D.C. bias winding around the core may be used to employ the full flux swing of the transformer's core. As an example, the transformer may utilize a core made of laminated iron.

The transformer 224 may advantageously be constructed to saturate if the pulse length exceeds a maximum prescribed value, thereby protecting a patient from excessive electrical energy. Preferably, the transformer 224 is capable of carrying 0.3 V-sec (3000 V×100 $\mu$sec) before saturation. Another advantage of the transformer 224 is that its output is floating, and no substantial current will flow if the patient is connected to ground potential. The secondary winding 224b is coupled to output connection nodes 230–231, which preferably connect to the cuvette holder device 10.

The load between the electrodes 40, 42 is represented by the in vitro implant agents and host material in the cuvette holder 10 which may contain platelets, human cells, red blood cells, mammalian cells, plant protoplasts, plant pollen, liposomes, bacteria, fungi, yeast, sperm, or other cells.

To protect the energy reservoir 220 and power supply 202, a diode 236 may be placed between the energy reservoir 220 and the connection 230. Likewise, to protect the energy reservoir 221 and power supply 220, a diode 237 may be placed between the secondary winding 224b and the connection 230.

Switches: The subsystem 200 also includes switches 226–227 to selectively enable current to flow through the primary and secondary windings 224a–224b, respectively. In one exemplary construction, each switch 226–227 may comprise an insulated gate bipolar transistor ("IGBT"), such as a Fuji Electric brand IMBI400F-060 model IGBT.

The switch 226 and the energy reservoir 221 are coupled in series, this series combination being attached in parallel with the primary winding 224a. When voltage is applied to a gate 226a of the switch 226, the collectors 226b and emitter 226c are electrically connected. Thus, the energy reservoir 221 is effectively placed in parallel with the primary winding 224a. This allows current from the energy reservoir 121 to flow through the primary winding 224a.

Similarly, the switch 227 and energy reservoir 220 are coupled in series, this series combination being attached in parallel with the secondary winding 224b. When voltage is applied to a gate 227a of the switch 227, the collectors 227b and emitter 227c are electrically connected. Thus, the energy reservoir 220 is effectively placed in parallel with the secondary winding 224b. This allows current from the energy reservoir 220 to flow through the electrodes 40, 42.

Advantageously, none of the energy reservoirs 220–221 or switches 226–227 grounds the windings 224a–224b. The windings 224a–224b, therefore electrically float. As a result, no substantial current will flow through a patient or other load 234 that is connected to another earth or ground potential.

Electroporation Pulse Controller: Another component of this example of the subsystem 200 is the power control 201, which manages operation of the switches 226–227. Broadly, the controller 66 (FIG. 2) regulates the on-times and off-times of the switches 226–227 in accordance a specified schedule, thereby generating a predetermined pulsing scheme at the electrodes 40, 42. When the control 201 triggers the switch 227, the voltage of the energy reservoir 220 is applied to the electrodes 40, 42. When the control 201 triggers the switch 226, the voltage of the energy reservoir 220 is applied to the transformer 224, where it is multiplied by six and applied to the connections 230–231. The controller 66 (FIG. 2B) may also trigger both switches 226–227 to apply an additive voltage, comprising the sum of the step voltages 208–209, to the electrode structures 40, 42.

Preferable Design Parameters: The electrical requirements can be derived from the field strength, which was determined efficacious from in vitro experiments with tumor cells and drugs, typically 1200–1300 V/cm, and a pulse length of about 100 $\mu$sec. The maximum voltage of the generator derives from the maximum cavity size used.

As an example, the material resistivity is assumed to be as low as 100 Ohm×cm. With an electrode area of 3 cm×3 cm=9 cm$^2$, the resistance is 22 Ohm. The internal impedance of the generator should be at least a factor 10 lower than 22 Ohm so that no substantial drop in voltage occurs between charging and delivered voltage. With the maximum voltage of 3000 V and a load impedance of 22 Ohm, the switching requirements from a partial capacitor discharge to generate a square pulse are a very substantial 400 kW.

The desired maximum permeation pulse length is 100 $\mu$sec; this results in an energy per pulse of 40 J. For the collection and electrophoresis pulse parameters, a maximum voltage of 500 V and maximum pulse length of 200 msec may be used.

The maximum load current is about 136 A, which translates into a primary current of 6·136=816 A, which the switch has to carry and turn on and off. The switches 226–227 can preferably maintain continuous current 800 A for one msec. The maximum voltage is 600 V. Transient spikes are limited to a maximum of 550 V for a 10% safety margin. This required careful low inductance mechanical assembly to reduce transients and to be able to get as close as safely feasible to the maximum voltage limit of the IGBT.

The load impedance of 22 Ohm is transformed to the primary: 22/6×6–0.61 Ohm. A total internal impedance of 0.055 Ohm was achieved on the primary side of the transformer, which translates to an equivalent impedance of 1.98 Ohm on the secondary. Such a low impedance can lead to excessive currents in case of an arc or short circuit and these would destroy the expensive switching IGBT. The IGBT can be configured to contain a current limiting feature, which turns the switch off within a few $\mu$sec in case of excessive load currents which might happen if an arc or a short circuit condition occurs. By inducing an arc in the secondary, we measured a benign shut down of the IGBT within 5 $\mu$sec, as soon as the current exceeds about 900 A in the primary, corresponding to 150 A in the secondary.

The necessary capacitor size can be estimated from the maximum allowable voltage drop across the load of 5%. The charge conducted in the primary pulse is 100 $\mu$s×816 A–0.08 Cb. If this should be 5% of the capacitor bank, the bank needs to hold 20×0.08=1.6 Cb. At 500 V maximum, the required capacity is C=Q/V=1.6/500=0.0032 F or 3200 $\mu$F. The energy stored in these capacitors is 400 Joule.

For the collection and electrophoresis pulse, a second capacitor discharge circuit delivers the longer pulse lengths (several 100 msec) and low voltage (500 V) without the pulse transformer. The low voltage circuit and the high voltage circuit are decoupled from each other by stacks of diodes 237 and 236.

In addition to the various hardware embodiments described above, a different aspect of the invention broadly concerns a method for generating a user-specified electric field pulsing pattern to achieve improved electroporation. Data Storage Media: This method may be implemented, for example, by operating the controller 66 to execute a sequence of machine-readable instructions. These instructions may reside in various types of data storage media. In this respect, one aspect of the present invention concerns an article of manufacture, comprising a data storage medium tangibly embodying a program of machine-readable instructions executable by a digital data processor to perform method steps to generate a user-specified electric field pulsing pattern to achieve improved electroporation.

Figure 5:
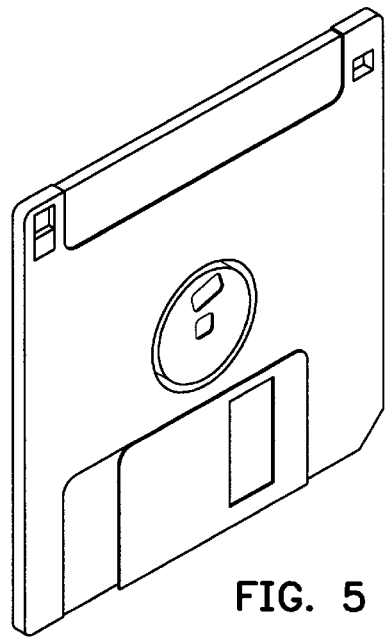
FIG. 5 is a diagram of an exemplary article of manufacture, comprising a data storage medium, in accordance with one aspect of the present invention.
Figure 6:
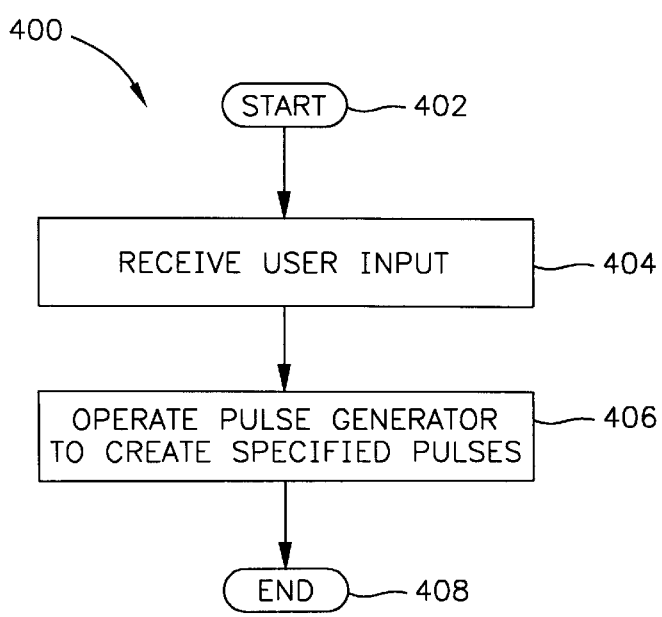
FIG. 6 is a flowchart illustrating an exemplary sequence of method steps in accordance with one aspect of the present invention.
Figure 7:
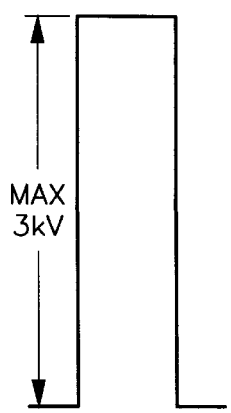
FIG. 7 is a drawing illustrative of an electroporation pulse, pursuant to the invention.

This data storage medium may comprise, for example, RAM contained within the controller 66. Alternatively, the instructions may be contained in another data storage medium, such as a magnetic data storage diskette (FIG. 5). Whether contained in the controller 66 or elsewhere, the instructions may instead be stored on another type of data storage medium such as DASD storage (e.g., a conventional "hard drive" or a RAID array), magnetic tape, electronic read-only memory (e.g., ROM), optical storage device (e.g., WORM), paper "punch" cards, or other data storage media. Operational Steps: As mentioned above, one aspect of the invention broadly concerns a method for generating a user-specified electric field pulsing pattern to achieve improved electroporation. FIG. 6 shows a sequence of method steps 400 to illustrate one example of this aspect of the present invention. For ease of explanation, but without any limitation intended thereby, the sequence of FIG. 6 is described in the context of the subsystem 200 described above.

After the steps 400 are initiated in task 402, the controller 66 in task 404 receives user input specifying an output pulse pattern of one or more output pulses. As an example, this user input may be received from the user interface 50. As an alternative, the user input may be received from another electronic device, or even a prestored record.

Preferably, the user input specifies a duration for each pulse and also specifying either a "high" output voltage or a "low" output voltage. Next, for each pulse of low predetermined voltage, the pulse generator in task 404 generates the "low" predetermined voltage at the output terminals 230 and 231 for the specified duration. More particularly, the controller 66 may generate a low voltage pulse by gating the switch 227, thereby permitting the energy reservoir 220 to discharge through the electrodes 40, 42.

Also, in task 404, high voltage pulses are generated at the secondary winding terminals by concurrently applying another voltage to the primary winding terminals of the transformer for the specified duration. More particularly, the high voltage pulse involves generating the voltage as discussed above, while concurrently triggering the switch 226 to permit the energy reservoir 221 to discharge through the primary winding 224. As the voltage of the reservoir 221 is multiplied by the transformer 224, a high voltage is created at the electrodes 230–231. This voltage is the additive sum of the voltages stored in the energy reservoirs 220–221. Alternatively, a lesser "high" voltage output may be created solely by triggering the switch 226, without involving the switch 227.

One or more of the above-mentioned pulses are therefore generated in task 404 to produce the user-specified pulse pattern. After the user-specified pulsing pattern is created completed in task 404, the routine 400 ends in task 406.

Operation With Exemplary Pulsing Pattern: As mentioned above, the pulse subsystem 200 provides a user-specified pulse pattern comprising one or more pulses of "high" and/or "low" output voltage. Other exemplary pulse shapes, which may be used alone or in combination to constitute the user-specified pulsing scheme is taught in the U.S. patent application Ser. No. 08/709,615, as discussed above. FIGS. 8–11 illustrate various exemplary pulse shapes, which may be used alone or in combination to constitute the user-specified pulsing scheme with associated temperature profile in real-time for processing of materials. The time scale is not necessarily linear as shown since the pulsing event occurs temporally in microseconds and cooling and heating of materials is an extrinsic factor of the apparatus used depending upon the receptacle device's volume for containing the materials and thermal design for effectuating heat transfer into or out of the receptacle device.

Although each of the pulsing patterns of FIGS. 8–11 may provide distinct advantages for different applications, the following description highlights the features and operation of a pattern 700 (FIG. 9) to illustrate the operation of the invention, both in the electroporation pulse scheme and temperature control in real-time. The polarity and current, which can be pulse width modulated, through the Peltier device 44 directly correlates with temperature in the receptacle device. In the cooling phase of the materials undergoing electroporation, temperatures are typically around four degrees centigrade at the lower extreme and can be warmed to around 40 degrees centigrade. Desired material temperatures associated with electroporation pulsing in real time of particular cells and implant agents is functionally related to the type of cells and implant materials used and the desired outcome of the processing. Such control can be user specified and stored in a programmable form on a data storage media such as that shown in FIG. 5 and be implemented using the electroporation and temperature controller 100.

The pattern 700 comprises a "stepped pattern," in that it provides first, second, and third voltage levels 702–704. One, two, or all of these voltages may be the same, if desired. The pulses have first, second, and third durations 706–708. In the present example, the first and third voltages 706, 708 provide a 500 V (D.C.), whereas the second voltage 707 provides 3000 V (D.C.). In an alternative embodiment, the user may specify a desired magnitude of electric field to be applied by the transformer 224, and a measurement of the gap between the electrodes 40, 42. In this case, the controller 66 may compute the appropriate voltage for the transformer 224 to generate in order to apply the desired electric field, for example by multiplying the electric field by the gap. In one embodiment, the gap measurement may be input by the user manually. Alternatively, the gap may be mechanically measured and electronically fed to the controller 66 by automated means such as shown in U.S. Pat. No. 5,439,440, which is hereby incorporated by reference in its entirety.

The efficiency of the implant agents to cells during electroporation processing is significantly dependent on the duration of cellular membrane permeabilization which has been discovered to be directly dependent on the temperature prior to, during and after pulsing application. Cellular permeability is modifiable by temperature changes. By raising the temperature, the permeability of the cellular wall is lowered. The lowering the ambient material temperature causes the permeability of the cellular material to increase.

During initial processing, temperature should be lowered to around ice cooled temperatures, e.g., 4 degrees centigrade. After pulsing, usually several minutes, the temperature of the materials should be raised to around 40 degrees centigrade to seal and anneal the cellular membrane. However, some cellular materials are very sensitive to temperature and cannot survive extreme temperature changes. In such cases, cellular manipulations need to be carried out at the optimal cell survival conditions.

The corresponding temperature profile in real time would exist and be controlled by the Peltier device 44 in the materials undergoing electroporation. The causal relationship of temperature effects when materials undergo electroporation has been studied and demonstrated that cellular membrane alterations do occur under varying temperature and electrical fields. In particular, this is taught in an article entitled "Studies on Electroporation of Thermally and IF Chemically Treated Human Erythrocytes," by Nanda et al. in Bioelectrochemistry and Bioenergetics, 34 (1994) 129–134. Temperature is a significant factor during electroporation processing of cells such as red blood cells with implant agents. When temperature increases during electroporation processing, effectiveness is significantly reduced. For example when using red blood cells, Increase in the temperature during electroporation from four to forty-three degrees Centigrade reduces electroporation efficiency by approximately 50%. Post pulse incubation of red blood cells at higher temperatures further reduces the electroporation effectiveness.

Figure 12:
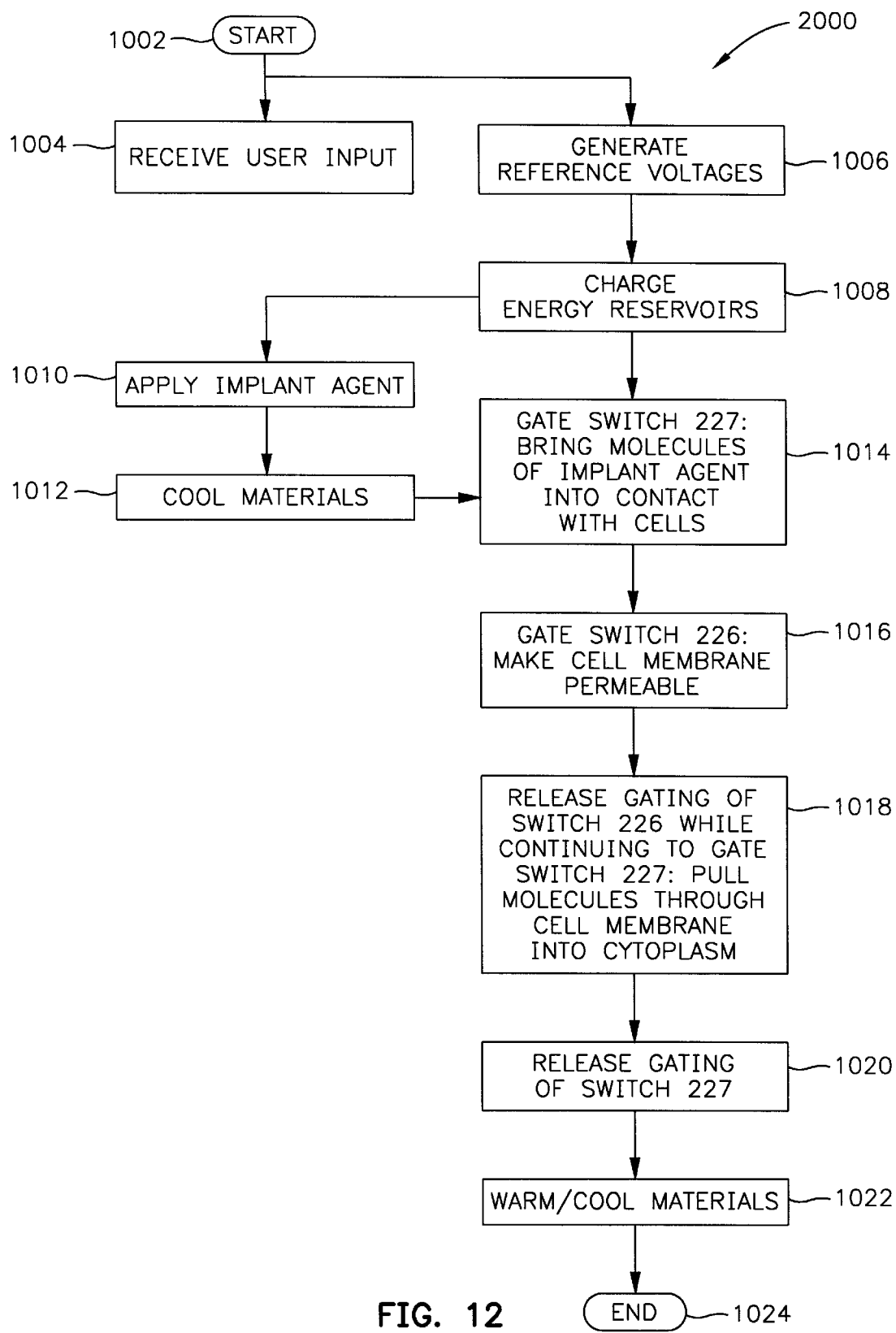
FIG. 12 is a flowchart illustrating an exemplary sequence of method steps in accordance with one example of the present invention.

FIG. 12 describes an illustrative sequence 2000 involved in generating and applying the step pattern 700, and the effects caused by application of the pattern 700 with corresponding control of temperature. After the sequence begins in task 1002, the user interface 50 receives user input in task 1004. In the illustrated embodiment, the user input includes the user's specification of a desired electroporation pulsing pattern, including a duration and voltage level for each pattern portion and the corresponding control of temperature.

Concurrently with task 1004, the power supply 202 generates the reference voltages at the output nodes 208–209. In the present example, the reference voltages 208–209 of 500 V (D.C.) are used. Generation of the reference voltages in task 1008 charges the energy reservoirs in task 1008.

After task 1008, an operator in task 1010 inserts molecules of an implant agent to the receptacle device for processing. The implant agent may comprise one or more types of DNA, genes, and/or various chemical agents.

Step 1010 places the implant agent between the interstices of the cells at the process site. Next, in task 1012 the Peltier device 44 cools the materials in the receptacle device to around ice temperatures for most processing applications. However, warming of materials undergoing processing can be implemented.

After task 1012, the controller 66 in task 1014 gates the switch 227, discharging the energy reservoir 220, thereby applying the "low" voltage to the electrodes 40, 42. This step accumulates molecules of the implant agent near the membranes of the cells in the cell sample. As discovered by the present inventors, this step may be adequately performed with a reduced voltage. Accordingly, the "low" voltage of the energy reservoir 220 achieves this purpose, while still avoiding damage to the cells in the sample and saving electrical energy.

Figure 9:
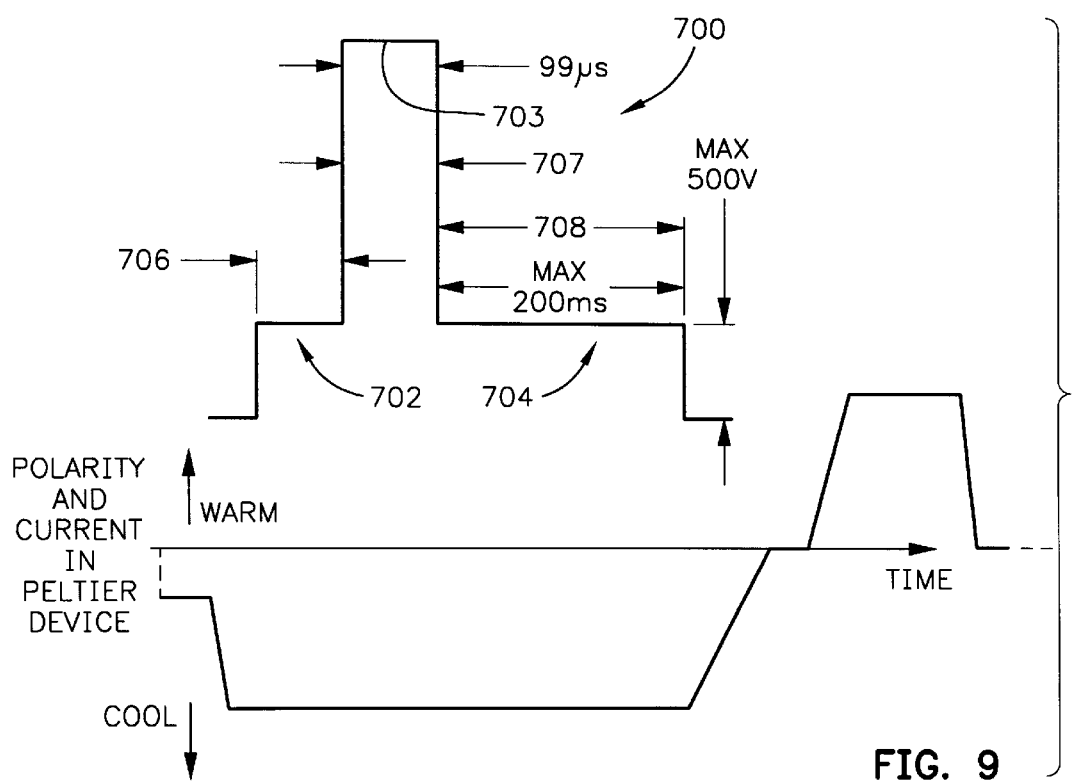

FIG. 9 illustrates task 1014 as the voltage pulse 702. As shown, this pulse preferably comprises a square wave having a duration 706 of about 10–200 msec and a voltage of about 500 V (D.C.). Depending upon the application, however, different parameters may be substituted to define the pulse 702. A corresponding cooling period occurs to allow greater permeability of cellular materials undergoing processing.

After task 1014, the controller 66 in task 1016 gates the switch 226 on (while continuing to gate the switch 227). This creates a "high" voltage upon the electrodes 40, 42, corresponding to the sum of the reference voltages 208–209. This high voltage is sufficient to safely create small pores in the cells of the tissue sample. FIG. 9 illustrates this step as the voltage pulse 703. As illustrated, this pulse preferably comprises a square wave having a duration 707 of about 100 $\mu$sec and an electric field magnitude of about 1200 V/cm. Depending upon the application, however, different parameters may be substituted to define the pulse 702. The temperature is maintained at the cool state during processing to maintain high permeability of a cellular membrane undergoing processing.

Advantageously, the subsystem 200 automatically limits damage to cells of the tissue sample during this step. In particular, when the voltage from the primary winding 224a saturates the secondary winding 224b, the voltage presented by the secondary winding 224b begins to decay, in accordance with known principles of transformer operation. Thus, even if the voltage applied to the primary winding 224a is applied for an excessive length of time, the secondary winding 224b automatically limits the tissue sample's exposure to this high voltage pulse.

Next, in task 1018 the controller 66 ceases gating of the switch 226 while continuing to gate the switch 227. This step permits the molecules of the implant agent to transit the cells' permeable membranes, and enter the cells' cytoplasm.

Figure 10:
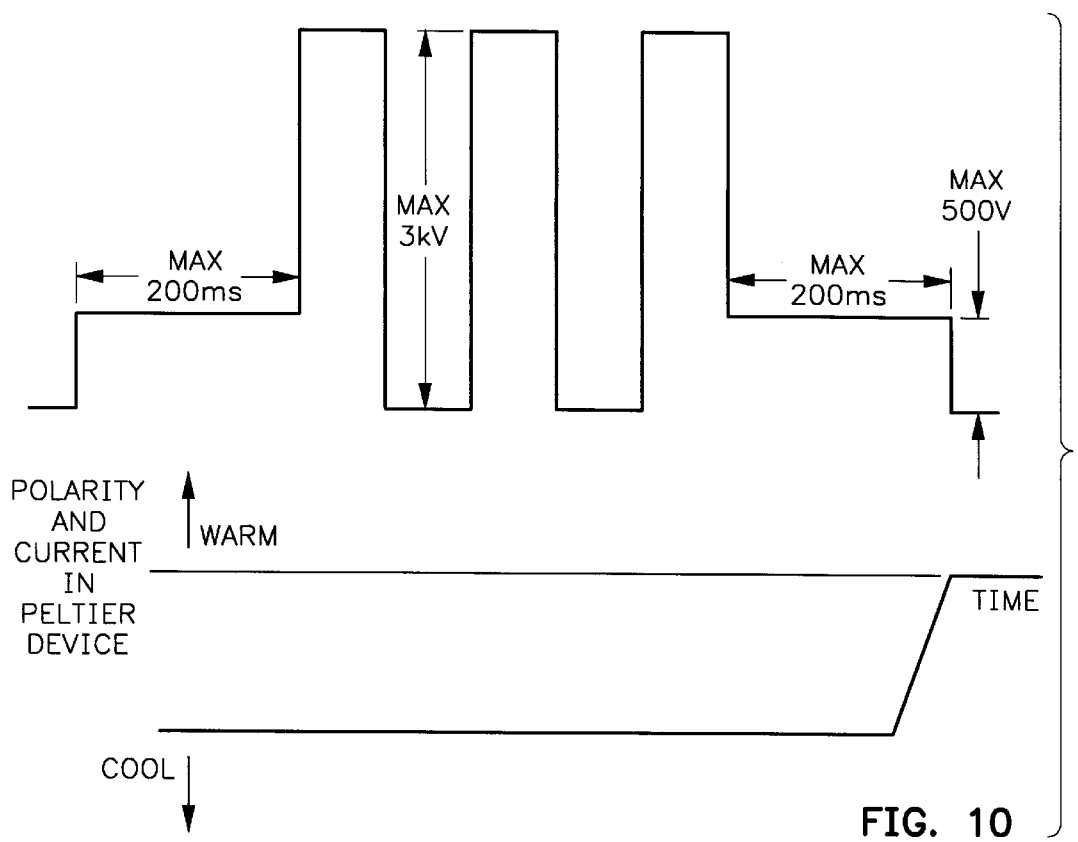
Figure 11:
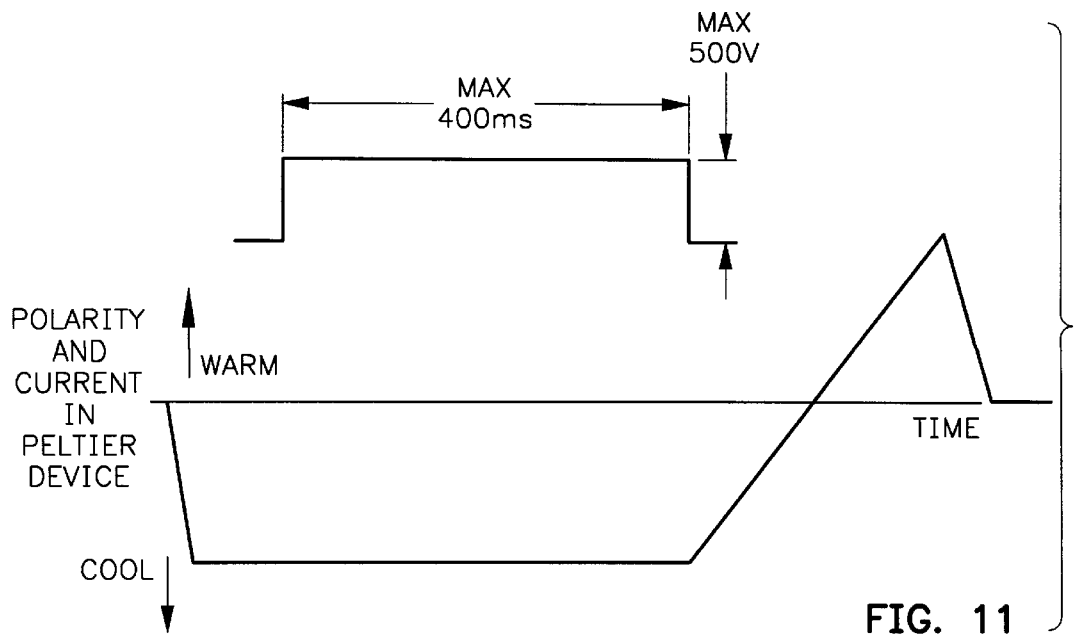

FIG. 10 illustrates this step as the voltage pulse 704. As illustrated, this pulse preferably comprises a square wave having a duration 708 of about 1–200 msec and a voltage of about 500 V (D.C.). Depending upon the application, however, different parameters may be substituted to define the pulse 704.

After task 1018, the controller 66 releases gating of the switch 227, ending the pulse 700. Then, the Peltier device 44 either warms or cools the material in the receptacle device in task 1022, and the sequence 2000 ends in task 1024. This step normally takes on the order of several minutes where it is either desirable to leave the cellular membrane open (keeping material cool) or sealing or annealing the cellular membrane (keeping the material warm).

Other uses of the invention provided herein include all electroporation mediated processes such as electrofusion, electroinsertion, electrochemotherapy, electrogene therapy and electrostimulation. While the presently preferred embodiments of the invention have been disclosed, it will be apparent to those skilled in the art that various changes and modifications can be made herein without departing from the scope of the invention as defined by the appended claims.

We claim:

1. An electroporation apparatus, the apparatus comprising:
   receptacle means for providing a) an interface to a voltage of specified output pulsing, and b) temperature control of materials undergoing electroporation disposed within;
   at least two spaced apart electrodes, at least one of the electrodes contains a Peltier device;
   at least one opening to provide transfer of the materials;
   a source of energy for energizing the at least two electrodes; and
   a controller constructed to receive user specification of an integrated output electroporation pulsing event with a corresponding temperature profile superimposed therewith, the controller responsive to the user specification to output gating signals to the source of energy to generate the specified output pulsing and required polarity and magnitude to the Peltier device at the at least two electrodes, whereby the Peltier device and the at least two electrodes enable temperature control and electroporation.

2. The apparatus of claim 1, the controller including a microprocessor and the user specification of the electroporation pulsing event and required temperature of the materials undergoing electroporation by superposition of the gating signals to power supplies for electroporation and temperature control.

3. An electroporation apparatus comprising:
   receptacle means for providing a) an interface to a voltage of specified output pulsing, and b) temperature control of materials undergoing electroporation disposed within;
   at least two spaced apart electrodes, at least one of the electrodes contains a Peltier device;
   at least one opening to provide transfer of the materials;
   a source of energy for energizing the at least two electrodes;
   a controller constructed to receive user specification of an integrated output electroporation pulsing event with a corresponding temperature profile superimposed therewith, the controller outputs gating signals to the source of energy to generate the specified output pulsing and required polarity and magnitude to the Peltier device at the at least two electrodes, whereby the Peltier device and the at least two electrodes enable temperature control and electroporation; and
   a user interface coupled to the controller for inputting the temperature profile.

4. The apparatus of claim 1, the electrodes comprising plate electrodes.

5. The apparatus of claim 1, further comprising:
   a gap sensor to sense a distance between the electrodes and provide a representative electronic gap distance output signal.

6. The apparatus of claim 1, wherein the controller and the energy source for generating the user specified electroporation pulse shape comprising:
   a first power supply to provide a first output voltage;
   a second power supply to provide a second output voltage, the first and second power supplies are separate sources of electrical energy;
   a transformer having electromagnetically coupled primary and secondary windings, the secondary winding being interposed between a pair of terminals;
   a first switch coupled to the first power supply and the primary winding and being responsive to a first gating signal to apply the first output voltage from the first power supply to the primary winding;
   a second switch coupled to the second power supply and the secondary winding and responsive to a second gating signal to apply the second output voltage from the second power supply to the secondary winding; and
   a controller to receive user specification of an output pulse shape and provide the first and second gating signals to generate the specified output pulse shape at the terminals.

7. An electroporation apparatus, comprising:
   a controller constructed to receive user specification of an integrated output electroporation pulsing event with a corresponding temperature profile superimposed therewith, the controller outputs gating signals to the source of energy to generate the specified output pulsing and required polarity and magnitude to the Peltier device at the at least two electrodes, whereby the at least two electrodes enable temperature control and electroporation;
   a gap sensor to sense a distance between the electrodes and provide a representative electronic gap distance output signal,
the controller being programmed to perform steps comprising:
   receiving an input specifying a desired electric field;
   receiving an input specifying an electrode gap distance; and
   calculating a first voltage to provide the specified electric field across the specified electrode gap distance.

8. The apparatus of claim 6, further comprising:
   a pair of electrodes electrically connected to predetermined contacts of the transformer;
   a gap sensor to sense an electrode gap distance between the electrodes and provide a representative electrode gap distance output signal;
   wherein the controller is further programmed to perform steps comprising:
      receiving an input of a desired electric field;
      receiving the electrode gap distance output signal; and
      computing the first voltage to provide the input desired electric field across the electrodes.

9. The apparatus of claim 1, wherein the controller and the energy source for generating the user specified temperature state during the electroporation pulsing event includes means for controlling polarity of electrical energy at the at least two electrodes from the controller that controls heat flow using the Peltier device.

10. The apparatus of claim 6, wherein the controller and the energy source includes means for controlling polarity and power magnitude to the at least two electrodes thereby controlling direction of heat transfer from the Peltier device, the controller includes a temperature sensor for closed loop control of the Peltier device.

11. An electroporation apparatus, comprising:
receptacle means for providing a) an interface to a voltage of specified output pulsing, and b) temperature control of materials undergoing electroporation disposed within;
at least two spaced apart electrodes, at least one of the electrodes contains a Peltier device;
at least one opening to provide transfer of the materials;
a source of energy for energizing the at least two electrodes;
a controller constructed to receive user specification of an integrated output electroporation pulsing event with a corresponding temperature profile superimposed therewith, the controller outputs gating signals to the source of energy to generate the specified output pulsing and required polarity and magnitude to the Peltier device at the at least two electrodes, whereby the Peltier device and the at least two electrodes enable temperature control and electroporation, wherein the receptacle means comprises a cuvette with at least one integral electrode contact surface attached to external surfaces of the cuvette, the at least one cuvette electrode is configured to slidably interface with and maintain positioning in a holder device, the holder device includes the at least one Peltier device in a complementary electrode structure that interfaces with at least one of the electrodes forming part of the cuvette, the holder has terminals with means for connection to the controller.

12. The apparatus of claim 11, wherein the cuvette is a non-flow type containing device.

13. The apparatus of claim 11, wherein the cuvette is a flow through containing device.

14. A receptacle device for electroporation in kit form, the kit comprising:
the receptacle device has at least two electrode structures for providing an interface to a specified output voltage pulsation waveform and heat transfer control for materials contained within the device;
at least one Peltier device forming a junction with at least one of the electrode structures; and
means for providing positional stability for the receptacle device and connecting the at least two electrode structures to a connectable external controller.

15. The kit of claim 14, the electrodes comprising plate electrodes.

16. A receptacle device for electroporation in kit form, the kit comprising:
the receptacle device has at least two electrode structures for providing an interface to a specified output voltage pulsation waveform and heat transfer control for materials contained within the device;
at least one Peltier device forming a junction with at least one of the electrode structures;
means for providing positional stability for the receptacle device and connecting the at least two electrode structures to a connectable external controller; and
a gap sensor to sense a distance between the electrodes and provide a representative electronic gap distance output signal.

17. A receptacle device for electroporation in kit form, the receptacle device has at least two electrode structures for providing an interface to a specified output voltage pulsation waveform and heat transfer control for materials contained within the device;
at least one Peltier device forming a junction with at least one of the electrode structures; and means for providing positional stability for the receptacle device and connecting the at least two electrode structures to a connectable external controller, wherein the receptacle device provides for liquid flow through and comprises:
an elongated flow through chamber having an inlet and an outlet at opposite ends thereof; and
a pair of elongated spaced apart parallel internal electrodes disposed in and extending along opposite sides of the chamber between the inlet and the outlet for fluid to flow between.

18. The kit of claim 17, wherein the receptacle device comprises a generally elongated non-conductive bar member having a rectangular cross section and an elongated through slot intermediate the ends thereof;
the electrodes are elongated flat conductive members sealingly applied to opposite sides of the bar member closing the slot and defining the elongated flow through chamber.

19. The kit of claim 18, wherein the inlet and the outlet are formed in one of the electrodes and communicate with opposite ends of the slot.

20. The kit of claim 19, wherein the receptacle device further comprises a generally U-shaped housing formed of a non-conducting material and having a pair of parallel side walls with an opening therebetween for removably receiving the flow through chamber.

21. The kit of claim 20, wherein the U-shaped housing includes slots in one side thereof for accommodating tubing connected to the inlet and the outlet.

22. The kit of claim 17, wherein the electrodes extend substantially the full length of the flow through chamber.

23. The kit of claim 22, wherein the flow through chamber comprises an elongated nonconductive tubular member;
a header on one end of the tubular member defining one of the inlet and the outlet; and
a pair of elongated conductive bars extending along opposite sides of the tubular member defining the electrodes.

24. The kit of claim 17, wherein the flow through chamber comprises an elongated conductive tubular member defining one of the electrodes, and a pair of headers on the ends of the tubular member defining the inlet and the outlet; and
a conductive rod extending coaxially of the tubular member defining the other of the conductors.

25. The kit of claim 17, wherein the flow through chamber substantially rectangular in cross section.

26. The kit of claim 25, wherein the flow through chamber comprises an elongated nonconductive tubular member;
a header on one end of the tubular member defining one the inlet and the outlet; and
a pair of elongated conductive bars extending along opposite sides of the tubular member defining the electrodes.

27. A method for regulating temperature of an electroporation pulse apparatus that includes a receptacle means for containing and controlling temperature of a material contained within, the receptacle means has an electrode structure that includes a Peltier device;

providing user input specifying an output pulse pattern of at least one output pulse for effectuating electroporation of the material, the user input specifying a duration for each pulse wherein the pulse pattern defines an event;

providing a second user input specifying an output pulse pattern for controlling temperature of the material via the Peltier device during the event.

28. The method of claim 27, the material comprising cells removed from a living being.

29. A method of electroporation using a cuvette holder comprising:

positioning a pair of electrodes containing a Peltier device relative to a region of cells;

applying at least one voltage pulse to the electrodes of specified polarity and delivering a predetermined implant agent to the region of cells at a specified temperature;

moving molecules of the implant agent toward the cells by applying at least one pulse at a second voltage to the electrodes for a second predetermined time;

creating pores in a plurality of the cells; and moving molecules of the implant agent into a plurality of the pores while controlling temperature.

30. The method of claim 29, the second predetermined magnitude of voltage providing a resultant electric field at the electrodes in the range of 300–3000 V/cm.

31. The method of claim 29, further comprising the steps of computing the second predetermined magnitude of voltage by multiplying a desired electric field by measurement of a gap existing between the electrodes.

* * * * *